US007877406B2

(12) United States Patent
Crucs

(10) Patent No.: US 7,877,406 B2
(45) Date of Patent: Jan. 25, 2011

(54) SYSTEM AND METHOD FOR NAME GRABBING VIA OPTICAL CHARACTER READING

(75) Inventor: Kevin M. Crucs, Akron, OH (US)

(73) Assignee: Apteryx, Inc., Akron, OH (US)

( * ) Notice: Subject to any disclaimer, the term of this patent is extended or adjusted under 35 U.S.C. 154(b) by 803 days.

(21) Appl. No.: 11/078,560

(22) Filed: Mar. 11, 2005

(65) Prior Publication Data

US 2006/0206457 A1    Sep. 14, 2006

(51) Int. Cl.
*G06F 17/30* (2006.01)
*G06F 3/048* (2006.01)

(52) U.S. Cl. .................. 707/772; 715/226; 715/804
(58) Field of Classification Search .............. 707/772, 707/779; 715/224–226, 804
See application file for complete search history.

(56) References Cited

U.S. PATENT DOCUMENTS

| 5,237,628 | A   | * | 8/1993  | Levitan ................ 382/175 |
| 5,903,631 | A   | * | 5/1999  | Smith et al. ............ 379/90.01 |
| 6,247,029 | B1  | * | 6/2001  | Kelley et al. ............. 715/507 |
| 6,249,283 | B1  | * | 6/2001  | Ur .......................... 715/764 |
| 6,321,224 | B1  | * | 11/2001 | Beall et al. ................. 707/5 |
| 6,662,310 | B2  | * | 12/2003 | Lopez et al. ............... 714/15 |
| 6,711,564 | B2  |   | 3/2004  | Crucs |
| 6,735,347 | B1  | * | 5/2004  | Bates et al. ............... 382/282 |
| 6,766,069 | B1  | * | 7/2004  | Dance et al. .............. 382/309 |
| 7,082,436 | B1  | * | 7/2006  | Bayiates ................... 707/102 |
| 7,735,017 | B2  | * | 6/2010  | Cunningham et al. ....... 715/770 |
| 2002/0023067 | A1 | * | 2/2002 | Garland et al. ............... 707/1 |
| 2002/0111962 | A1 | * | 8/2002 | Crucs ....................... 707/505 |
| 2003/0223637 | A1 | * | 12/2003 | Simske et al. .............. 382/176 |
| 2004/0205530 | A1 | * | 10/2004 | Borg ........................ 715/507 |

FOREIGN PATENT DOCUMENTS

WO    WO 2004051532 A1  *  6/2004

OTHER PUBLICATIONS

Microsoft Corporation. "Microsoft® Computer Dictionary" May 1, 2002. Fifth Edition. Microsoft Press. 4 selected pages.*

* cited by examiner

*Primary Examiner*—John R. Cottingham
*Assistant Examiner*—James E. Richardson
(74) *Attorney, Agent, or Firm*—Hahn Loeser & Parks LLP

(57) ABSTRACT

A system and method for generating text data from graphical image information of a first data form and passing the generated text data to another data form is disclosed. The system comprises a computer-based platform configured to obtain search criteria data from a current data form of interest and search an operating system of the computer-based platform for at least one other data form having first data that match the search criteria data to identify any matching data forms. The computer-based platform is further configured to perform an image capture operation on at least one predefined area of any matching data forms to form at least one captured image. An optical character reading operation is performed on the at least one captured image to generate at least one instance of second data and the at least one instance of second data is passed to the current data form of interest.

28 Claims, 6 Drawing Sheets

FIG. 2

SYSTEM AND METHOD FOR NAME GRABBING VIA OPTICAL CHARACTER READING

TECHNICAL FIELD

Certain embodiments of the present invention relate to searching for information in a plurality of applications, windows, or data sets. More particularly, certain embodiments of the present invention relate to a system and method for searching for information in the form of graphical image information and converting the graphical image information to text data to bridge to, activate, or open another application, window, or data set.

BACKGROUND OF THE INVENTION

Each year there is an increase in the amount of computer automation for the home and office. Typically, such increases occur in discrete software applications that are specific to a desired goal or objective. For example, there are individual applications for billing, payroll, word processing, time keeping, inventory tracking, and personal organization. Each of these applications can be implemented and distributed by a different vendor and loaded onto a single computer.

User applications typically share compatibility and operability with an operating system that controls the computer. Typical examples of operating systems are Windows 95™, Windows 98™, Windows 2000™, and Windows NT™ available from Microsoft Corp., Linux™ available from Red Hat, OS/2 available from IBM Corp., and the Apple Macintosh Operating system available from Apple Computer, Inc. Thus, each application installed onto the computer must be able to run on the operating platform supporting the computer.

Operating systems available today allow a user to have more than one application running (loaded or open) simultaneously. This is also called multi-processing. Before opening (or launching) an application, it is in an "unloaded" state, stored in permanent or long term storage/memory. When an application is "launched", it becomes the "active" application. If another application is launched, a loaded and active application remains loaded but becomes "inactive". Thus, multiple applications may be loaded and "running" at any one time. However, unless the computer has multiple processors (CPUs), only one application is actually "active" at a time.

One problem many users face when using a plurality of applications, windows, or data sets is that of switching between the various applications, windows, or data sets that are running simultaneously. For example, suppose a user is obtaining data about a patient from a practice management application in a doctor's office and wants to look at that patient's digitally stored x-ray images. The user must open or re-activate the x-ray image application, window, or data set; enter some search term that designates the patient; and wait for the application, window, or data set to return with the patient's x-ray images in the appropriate window. Thus, even though the user has the patient's identifying data in the practice management application that he/she is viewing, the user must open or activate the x-ray imaging application, and must then enter a query to locate and obtain the window containing the desired data. These additional operations can be time-consuming if the user is processing multiple patients per day.

The burden of having to manually enter data when the required data is available to the user in another window, application, or data set is compounded when certain applications, windows, or data sets require multiple pieces of data. For example, some applications, windows, or data sets require both a name and a social security number in order to distinguish between patients having the same name. In this example, the different social security numbers distinguish between the files of these two patients and their respective related information. Thus, even if a user is viewing a particular patient's profile in a patient management application and has the patient's social security number on screen, the user will still be required to type in the social security number, in addition to the patient's name, in the other desired application such as an x-ray imaging application. Some Windows™ programs allow a user to "cut-and-paste" information from one window to another. However, this method is time consuming when several fields of data need to be re-entered.

There is also a need to open a plurality of files across a plurality of applications, windows, or data sets in a network environment. In such a network environment, a first user could open one window in one application where that one window contains data useful to a plurality of other users on the network. It is desirable for the other users to access that data from the one window in the one application and use it to open other windows in other applications, instead of being forced to click on a plurality of boxes and/or type in the needed key data to open a file.

In addition, in either a single PC operation or a network operation, there is a need for a user to integrate a new application, window, or data set with existing applications, windows, or data sets. In this manner, it would be desirable for a user to purchase a new application and integrate the data residing in files in an existing application, window, or data set to create new files in the new application, window, or data set.

U.S. Pat. No. 6,711,564, issued to Crucs on Mar. 23, 2004, is incorporated herein by reference in its entirety. U.S. Pat. No. 6,711,564 describes a method and system for extracting data that is associated with one application, window, or data set and bridging that data to another application, window, or data set. The particular data form (application, window, or data set) is located using search criteria derived from a first active data form (application, window, or data set). If the particular data form is located in an unloaded (not running) application, window, or data set the requisite data form (e.g., application, window, or data set) is launched and made active. The necessary data is provided to the application, window, or data set to retrieve the particular window or data set of the data form. If the particular data form is located in a loaded application, window, or data set, the necessary data from the first data form is bridged into the loaded application, window, or data set. The necessary data to be bridged pre-exists in the form of text data within the application and is known by the operating system.

The system and method of U.S. Pat. No. 6,711,564 allows data to be extracted from the title bar or text associated with a window in another application. On many operating systems, a window (whether a main application window, title bar, or control) is defined by both its content and an operating system identifier (e.g., a class name). Using the window content and/or identifier, the system is able to search through a list of windows currently existing in an operating system (including child windows) for windows matching the desired criteria. Once the desired window is located, the relevant data can be extracted and used in the new application.

One disadvantage of the system and method of U.S. Pat. No. 6,711,564 is that, if a target window is a custom drawn window (e.g., a custom graphic window), the text data associated with that target window may be different from the information actually displayed in the custom drawn window. That is, each window class can have its drawing capabilities overridden by the underlying control class written by a company/developer in order to permit custom drawing of the window. With such styles, the window text data associated with the window in the operating system may not necessarily reflect the information displayed in the actual target window. Therefore, the desired information does not exist as data that can be extracted by the system and method of U.S. Pat. No. 6,711,564.

It is desirable to be able to bridge information between applications, windows, or data sets, even though the information may only initially exist as an image such as a custom graphic drawing.

Further limitations and disadvantages of conventional, traditional, and proposed approaches will become apparent to one of skill in the art, through comparison of such systems and methods with the present invention as set forth in the remainder of the present application with reference to the drawings.

BRIEF SUMMARY OF THE INVENTION

A first embodiment of the present invention provides a computer-implemented method for automatically generating and bridging data into a current data form of interest in response to searching an operating system. The method includes obtaining search criteria data from a current data form of interest and searching an operating system for at least one other data form having first data that match the search criteria data in order to identify any matching data forms. The method further includes performing an image capture operation on at least one predefined area of the matching data forms to form at least one captured image. The method also includes performing an optical character reading operation on the at least one captured image to generate at least one instance of second data. The method further includes passing the at least one instance of second data to the current data form of interest.

Another embodiment of the present invention comprises a system for automatically generating and bridging data into a current data form of interest in response to searching an operating system of the system. The system comprises a computer-based platform configured for obtaining search criteria data from a current data form of interest and searching an operating system for other data forms having first data that match the search criteria data in order to identify any matching data forms. The computer-based platform is also configured for performing an image capture operation on at least one predefined area of the matching data forms to form at least one captured image. The computer-based platform is further configured for performing an optical character reading operation on the at least one captured image to generate at least one instance of second data. The computer-based platform is also configured for passing the at least one instance of second data to the current data form of interest.

These and other advantages and novel features of the present invention, as well as details of an illustrated embodiment thereof, will be more fully understood from the following description and drawings.

BRIEF DESCRIPTION OF SEVERAL VIEWS OF THE DRAWINGS

FIG. 2 is a schematic representation of an exemplary embodiment of two parent windows, in accordance with various aspects of the present invention.

DETAILED DESCRIPTION OF THE INVENTION

For purposes of describing embodiments of the present invention, the following definitions are to be used and, if necessary, supercede any commonly understood definition of the term.

Data Form—a data form is any collection of data or information. Included within a data form are computer programs or applications that are organized forms of data that control a computer to perform certain tasks and functions. Examples of data forms are applications, windows, data sets, and data field windows.

Window—a window is a graphic feature that allows a user to view information and provide information to a computer/application. A window may be a part of many applications. A Data Form may be presented as a window, for example.

Text Data—text data may include alphabetic data, numeric data, alpha-numeric data, or any other symbol character data, but not graphical image data.

Figure 1:
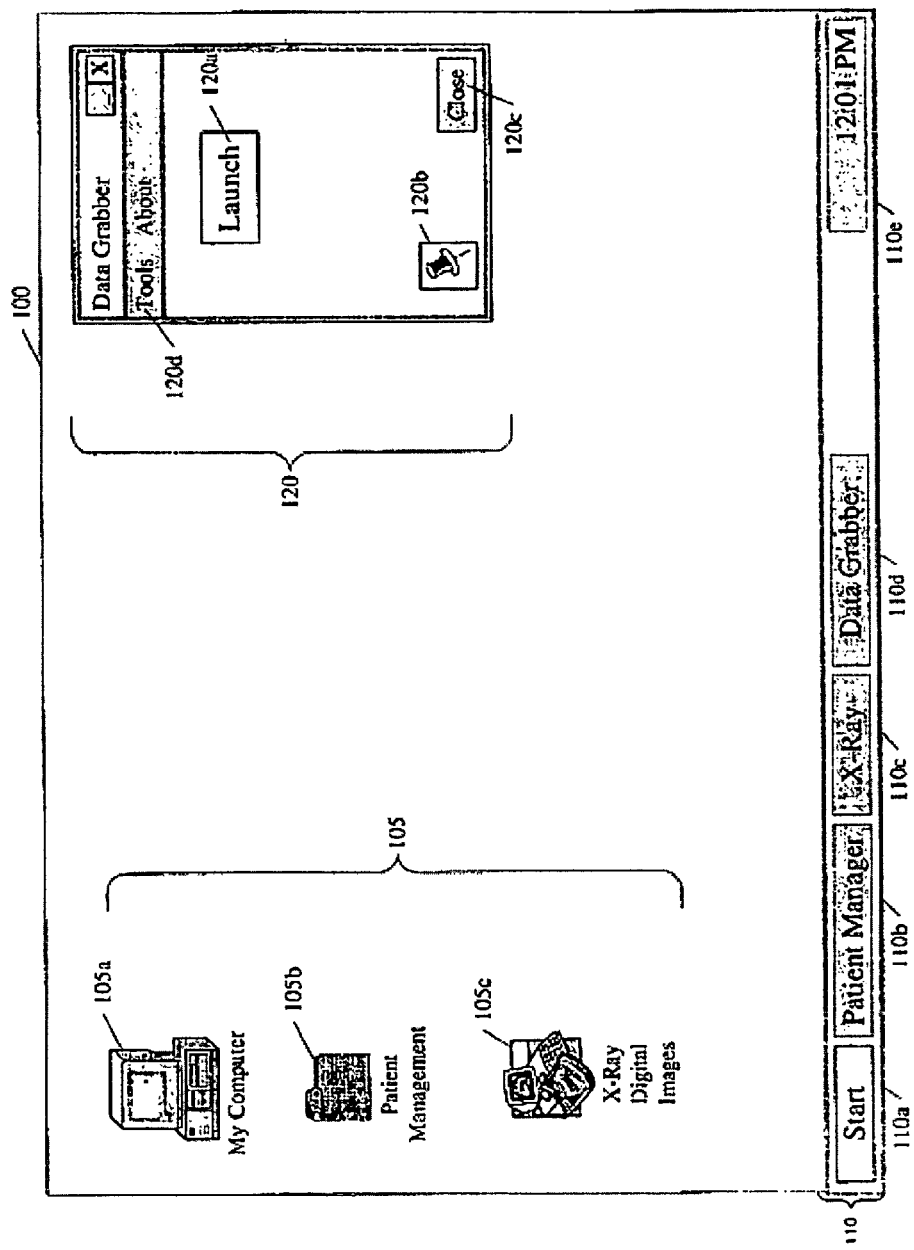
FIG. 1 is a screen shot of an embodiment of the present invention, in accordance with various aspects of the present invention.

FIG. 1 is an exemplary sample screen from a computer using the Windows NT™ operating system, in accordance with an embodiment of the present invention. The entire screen is designated by the reference number 100. Within screen 100 are shortcuts to specific applications 105. In this exemplary screen 100, there are three individual shortcuts 105 to three different applications. In this context, a shortcut is a link represented by a stylized icon that appears on the desktop of the operating system and allows the user to launch an application by double-clicking on that shortcut. The first shortcut 105a is a standard shortcut with the Windows NT™ operating system called "My Computer" and allows a user to view data in the various media drives associated with the computer. Shortcut 105b is a shortcut to an application for entering, editing, viewing, and maintaining patient files. Shortcut 105c is a shortcut to an application for creating and managing patient x-rays.

The task bar (including Start Menu and System tray) 110 is part of the operating system. Depending on the operating system version, the task bar comprises a plurality of buttons and/or icons representing both executing (loaded) and non-executing (unloaded) applications available to the user. Some buttons expand to menus, for instance the Start Menu, when one clicks on them. Start button 110a is a standard feature of the Windows NT™ operating system. Button 110b relates to the patient management application described above in conjunction with shortcut 105b. Button 110c relates to the x-ray imaging application described above in conjunction with shortcut 105c. Button 110d relates to an embodiment of the present invention described herein. Area 110e is part of the System Tray (Systray) and comprises shortcut icons for a plurality of common system tools and applications, such as printer status when printing a document, and a clock. It should be noted that, in other embodiments of the present invention, the method of an embodiment of the present invention can be launched from an icon located in, for example, area 110e.

Buttons 110b-110d allow the user to switch between the described applications, windows, or data sets, e.g., changing the active/inactive status of an application that is running (loaded) by clicking on the associated button. In accordance with an embodiment of the present invention, active means that the application, window, or data set has been downloaded from permanent or long term storage, such as a hard drive or swap file, into the computer's RAM and is ready for use by the user. When the user clicks on a particular button, the current active application, window, or data set remains loaded into memory, but is sent to the background (made inactive). This means that the application, window, or data set remains in the computer's RAM, but the user is unable to interact with it until the application, window, or data set is reactivated. In some cases, the application will be swapped to temporary space on the hard drive (swap space) rather than remain in RAM, if RAM is limited. By clicking on these buttons, the user may toggle between various applications, windows, or data sets, making one active and causing the others to be deactivated. This makes it easier for the user to switch between the various applications, windows, or data sets. It should be noted that embodiments of the present invention are limited neither to the types of applications, windows, or data sets, nor to the number of applications, windows, or data sets shown in FIG. 1.

FIG. 1 also demonstrates yet another implementation in which a user may launch an embodiment of the present invention. Window 120 is a "sliding window" that can be used to execute an embodiment of the present invention. To bring this window into view, the user slides the cursor, using a mouse or a touchscreen, over to the top right side of window 100. Note that the activating location "top right" is not fixed, and it would be apparent to one skilled in the art how to modify the activating location on the screen to another area of the display. When the cursor "exits" the viewing area to the top right, window 120 slides into view. If the user moves the cursor back into the viewing area of window 100 but outside of window 120, the window 120 slides back out of view. When slid into view, the user may then launch an embodiment of the present invention by clicking on the "Launch" button 120a.

If the user wishes to tack the sliding window 120 into a fixed location on the screen, he/she may do so by clicking on button 120b (stylized as a push-pin). Button 120b operates so as to tack window 120 into position regardless of the mouse location. If the user does not wish to execute the program which implements an embodiment of the present invention, he/she may click on the "Close" button 120c. The "Tools" executable menu 120d allows the user to modify and customize the application and window descriptions.

Figure 2:
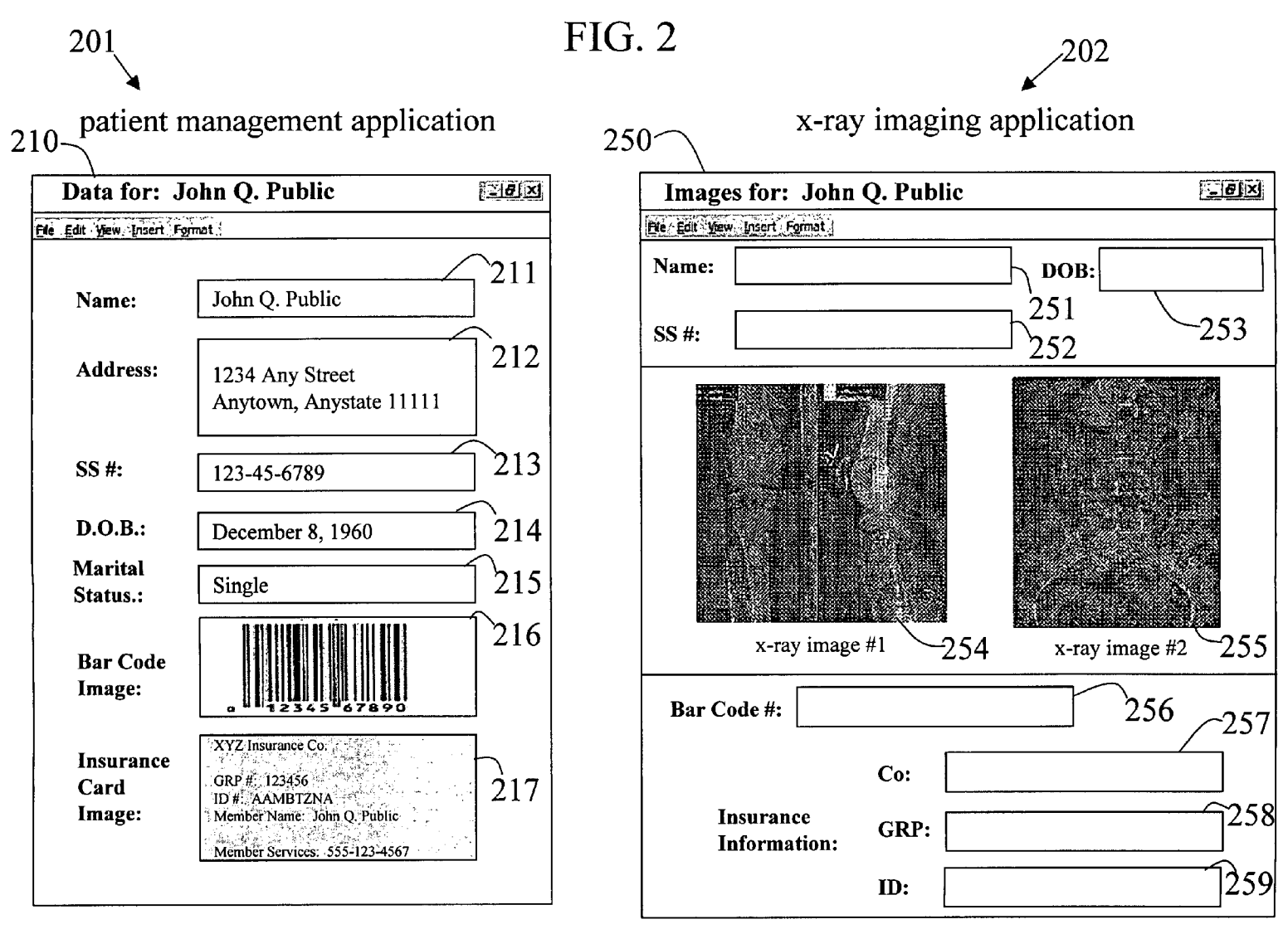

FIG. 2 is a schematic representation of an exemplary embodiment of two parent windows 210 and 250 of an operating system on a computer-based platform, in accordance with various aspects of the present invention. Parent window 210 is a window for a patient management application 201, and parent window 250 is a window for an x-ray imaging application 202. Parent window 210 includes child windows 211-217. Parent window 250 includes child windows 251-259. Child windows 211-215 include pre-existing text information for a patient ("John Q. Public") which is associated with the corresponding windows by the operating system 480 (see FIG. 4).

Embodiments of the invention described in U.S. Pat. No. 6,711,564 are able to extract the associated text information in windows 211-215 for inputting into windows in another application (e.g., windows 251-253 in the x-ray imaging application 202). Child windows 216 and 217, however, include custom graphic images (e.g., a bar code image and a scanned image of an insurance card). The bar code image in window 216 may represent a unique identifier for the patient in addition to the patient's social security number. The bar code image may be used to print bar code labels to be adhered to medications of the patient, for example. The insurance card image in window 217 is simply an image of the patient's insurance card which was scanned into the patient management application 201. The information in the insurance card image is typically used for billing of the patient's insurance company.

In the operating system 480 (see FIG. 4), there may be text associated with the windows 216 and 217. However, this text is not displayed and is different from the information conveyed by the images displayed in the windows 216 and 217. As a result, embodiments of the invention described in U.S. Pat. No. 6,711,564 cannot extract information contained in the images displayed in windows 216 and 217. However, embodiments of the present invention can, as will be described herein.

Figure 3:
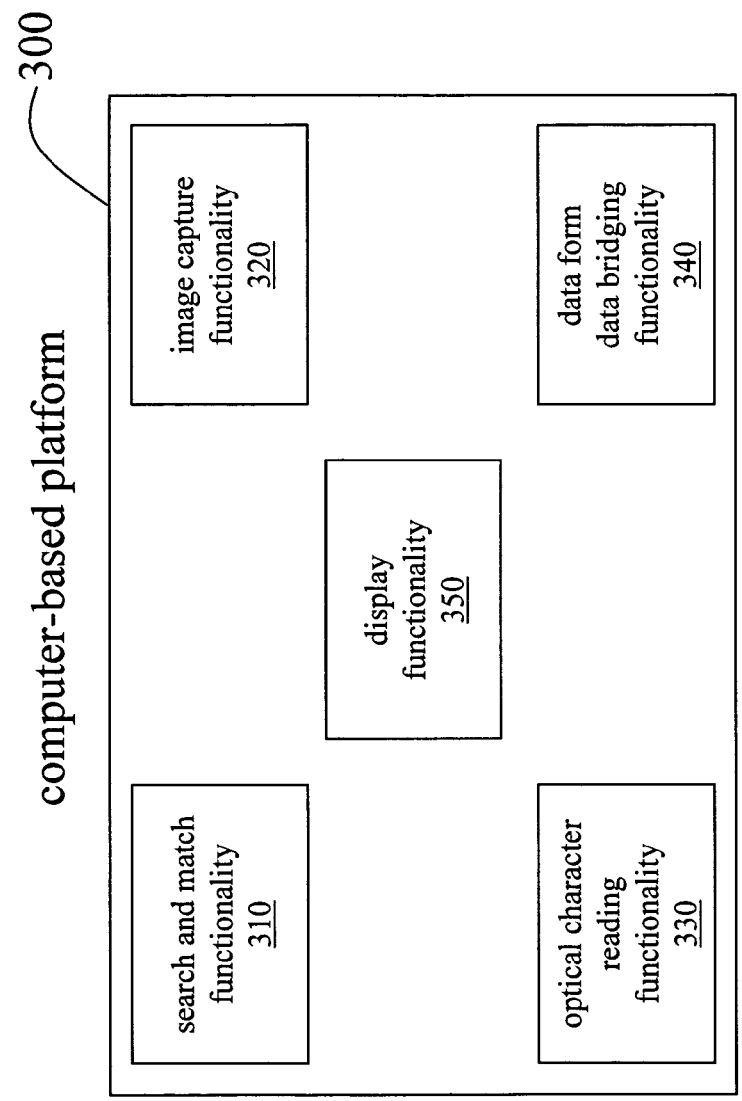
FIG. 3 is a functional block diagram of an exemplary embodiment of a computer-based platform, in accordance with various embodiments of the present invention.

FIG. 3 is a functional block diagram of an exemplary embodiment of a computer-based platform 300, in accordance with various aspects of the present invention. The computer-based platform 300 implements various functions, in accordance with an embodiment of the present invention. The various functions includes search and match functionality 310, image capture functionality 320, optical character reading functionality 330, data form data bridging functionality 340, and display functionality 350. Other functionalities are possible as well but are not shown in FIG. 3.

Figure 4:
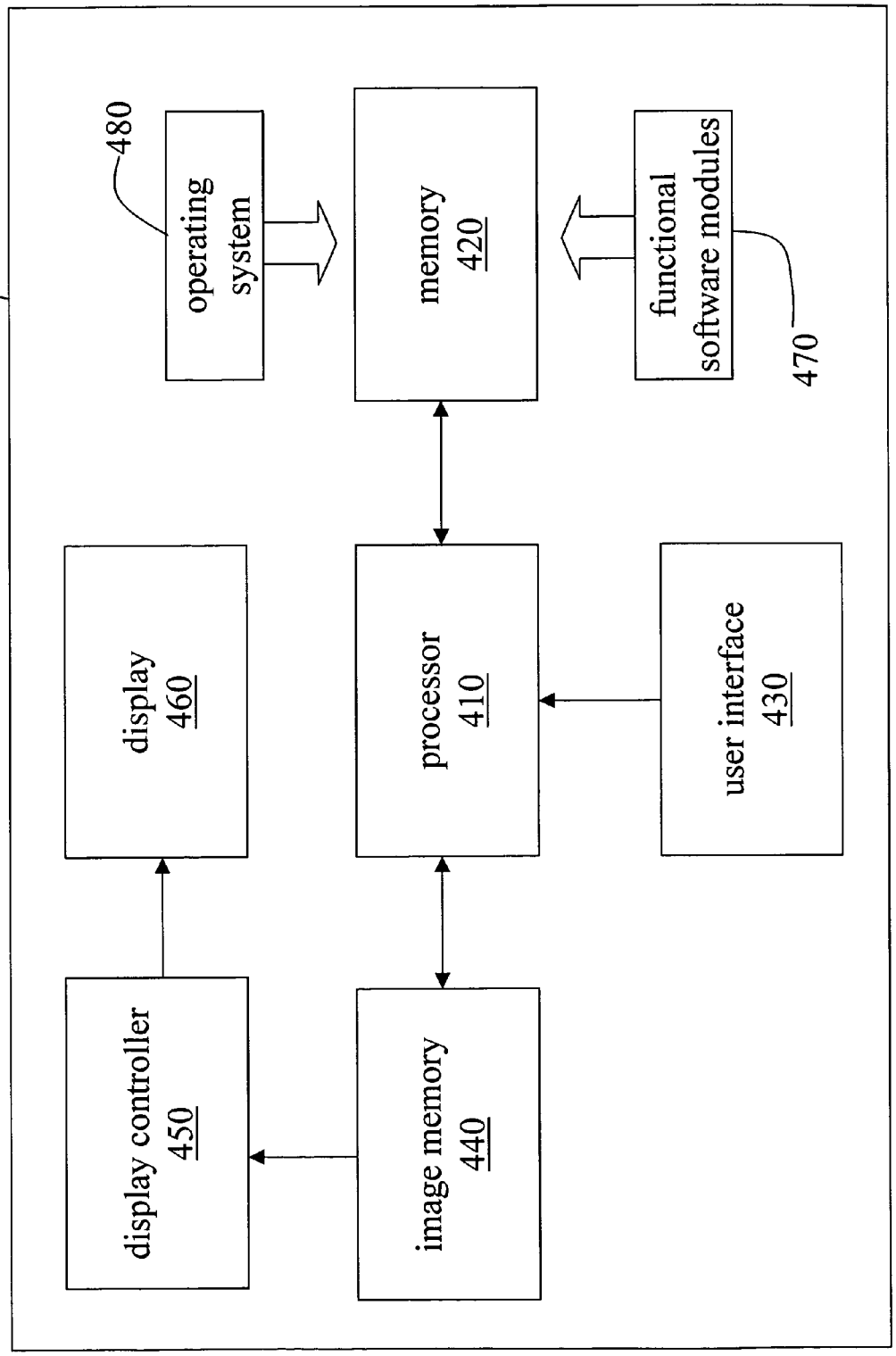
FIG. 4 is a schematic block diagram of an exemplary embodiment of the computer-based platform of FIG. 3 implementing the functionality of the computer-based platform of FIG. 3, in accordance with various aspects of the present invention.

FIG. 4 is a schematic block diagram of an exemplary embodiment of the computer-based platform 300 of FIG. 3 implementing the functionality of the computer-based platform 300 of FIG. 3, in accordance with various aspects of the present invention. The computer-based platform 300 comprises a processor 410, a general memory 420, a user interface 430, an image memory 440, a display controller 450, and a display 460. The computer-based platform 300 includes an operating system 480 and functional software modules 470. The processor 410 interfaces to the memory 420, user interface 430, and image memory 440. The display controller 450 interfaces to the image memory 440 and the display 460. The operating system 480 is loaded into memory 420 and is executed by processor 410. The functional software modules 470 are loaded into memory 420 and are executed by the processor 410. The functional software modules 470 perform the functionalities 310-350 of FIG. 3.

Figure 5:
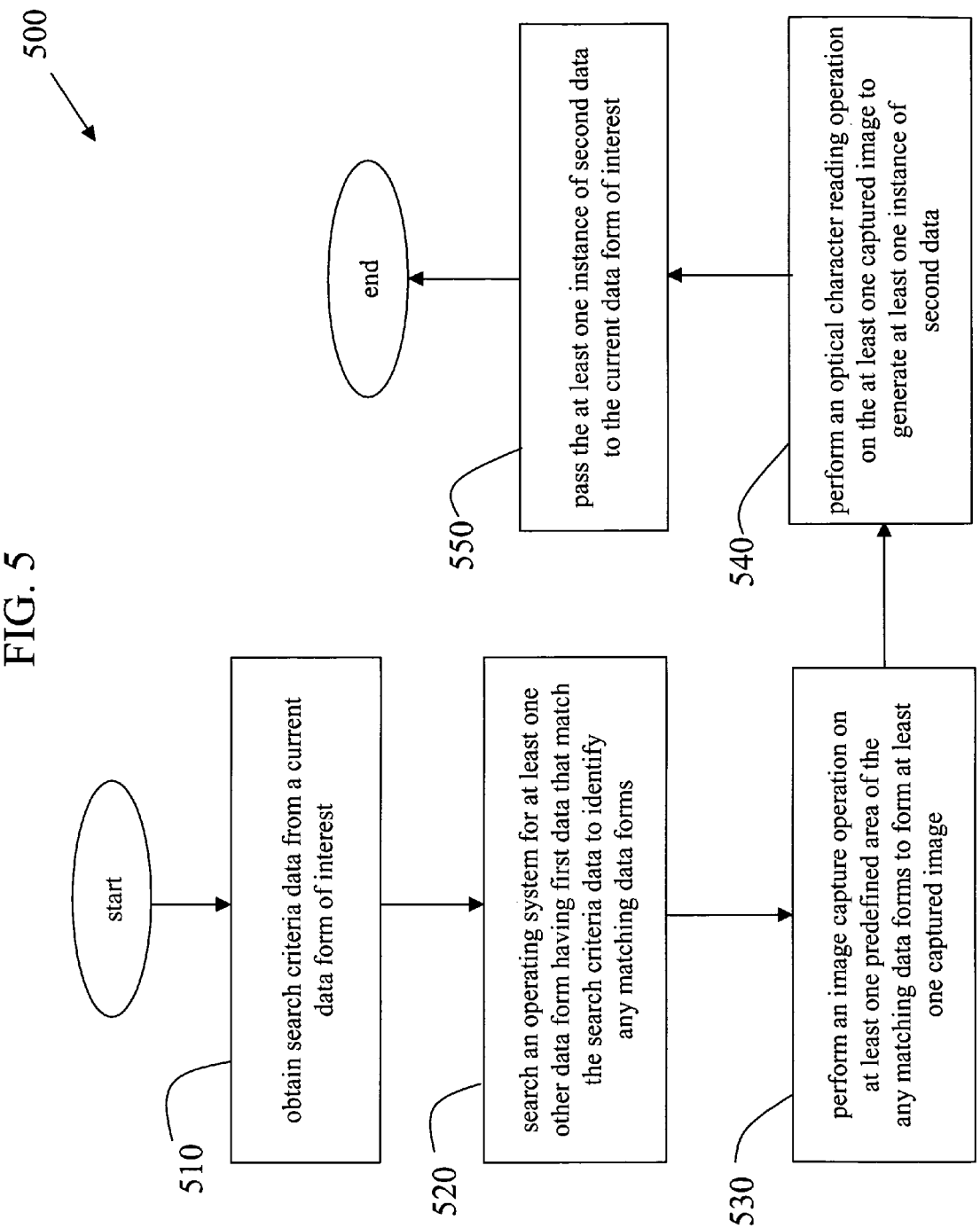
FIG. 5 is a flowchart of an embodiment of a method executing the functionality of the computer-based platform of FIG. 3 on the computer-based platform of FIG. 4, in accordance with various aspects of the present invention.

FIG. 5 is a flowchart of an embodiment of a method 500 executing the functionality of the computer-based platform 300 of FIG. 3 on the computer-based platform 300 of FIG. 4, in accordance with various aspects of the present invention. In step 510, search criteria data is obtained from a current data form of interest. In step 520, a search operation is performed on an operating system for at least one other data form having first data that match the search criteria data to identify any matching data forms. In step 530, an image capture operation is performed on at least one predefined area of the matching data forms to form at least one captured image. In step 540, an optical character reading operation is performed on the at least one captured image to generate at least one instance of second data. In step 550, the at least one instance of second data is passed to the current data form of interest.

Embodiments of the present invention include definition files for each data form. These definition files define the search criteria and associated information to be obtained from other data forms. For example, the definitions for the current data form of interest (e.g., current application window) define all of the possible target information that the user may want to obtain. These definition files are predefined as part of the embodiment of the present invention. However, certain embodiments of the present invention may allow a user to modify the definition files.

As an example, referring again to FIG. 2, a user of the computer-based platform 300 may enter the x-ray imaging application 202, using the computer-based platform 300 and open a file resulting in displaying the window 250. The file is for the patient "John Q. Public" and was previously created and saved upon taking two x-ray images of the patient "John Q. Public" to digitally store the two images as "x-ray image #1" 254 and "x-ray image #2" 255. The user now needs to complete the file by entering data into the windows 251-253 and 256-259. However, the user is fairly sure that the desired information already exists in another file in the patient management application 201.

The user then clicks on the data grabber icon 110*d* (see FIG. 1) to launch the functionality of an embodiment of the present invention as described for FIG. 3. As a result, the method 500 of FIG. 5 is executed on the computer-based platform 300. The current data form of interest is the window 250. The method 500 obtains the search criteria data from the window 250. The search criteria data may include name (text) data, window class data, and/or control identifier (ID) data of the current data form of interest as described in U.S. Pat. No. 6,711,564 which is incorporated by reference herein in its entirety. Every window data form has at least a window class but may also have a name string and an ID.

The operating system 480 of the computer-based platform 300 is searched for any matching data forms (applications, windows, data sets) and finds a matching data form (e.g., parent window 210) in the patient management application 201. The text data associated with the child windows 211, 213, and 214 is bridged over to or passed to (e.g., input into) the corresponding child windows 251-253 of the parent window 250 (i.e., the current data form of interest) of the x-ray imaging application 202 as described generally in U.S. Pat. No. 6,711,564 and as shown specifically in FIG. 6. As defined herein, text data may include alphabetic data, numeric data, alpha-numeric data, or any other symbol character data, but not graphical image data. The child windows 256-259 also need to be filled with the appropriately corresponding data. However, the information needed for the windows 256-259 does not exist as text data that is associated with the windows 216 and 217 by the operating system 480. Instead, the information needed is represented as images or graphics within the windows 216 and 217.

Therefore, the functionality of an embodiment of the present invention performs an image capture operation (e.g., a print screen operation) on the appropriate areas of the window 216 and the window 217 to capture images of the needed information. The appropriate areas are also defined in the definition files and the operating system 480 defines the location of the graphics on the screen. Then, the embodiment of the present invention performs an optical character reading operation on the captured images to generate corresponding instances of text data. Optical character reading is well-known in the art. Again, as defined herein, text data may include alphabetic data, numeric data, alpha-numeric data, or any other symbol character data. The generated text data is then bridged over to or passed to (e.g., input into) the appropriate corresponding child windows 256-259 of the x-ray imaging application 202 as shown in FIG. 6.

For example, the graphic number information "1234567890" in the bar code image in window 216 is converted to numeric text data by the optical character reading functionality 330 and input into the window 256. The graphic alphabetic information "XYZ Insurance Co." in the window 217 is converted to alphabetic text data by the optical character reading functionality 330 and input into the window 257. The graphic numeric information "123456" in the window 217 is converted to numeric text data by the optical character reading functionality 330 and input into the window 258. The graphic alphabetic information "AAMBTZNA" in the window 217 is converted to alphabetic text data by the optical character reading functionality 330 and input into the window 259.

Certain embodiments of the present invention include both the ability to bridge over pre-existing text data already associated with a window and the ability to first generate text data from a pre-existing image or graphic and then bridge over the generated text data, which is initiated by the user in a single act. However, certain other embodiments may implement the two capabilities as separate functions that are initiated separately by the user.

Figure 6:
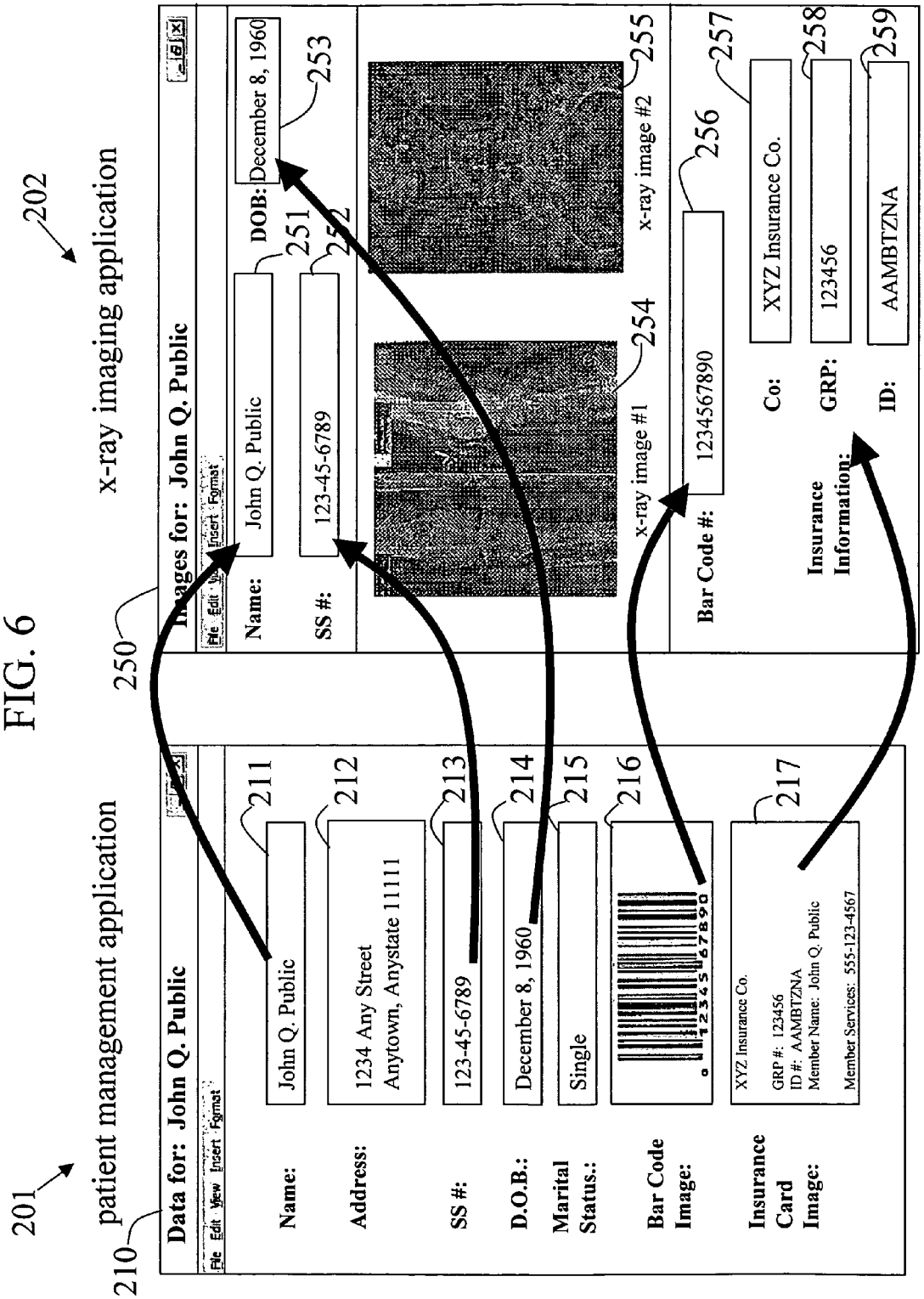
FIG. 6 is a schematic representation of the exemplary embodiment of the two parent windows of FIG. 2 showing data being bridged, in accordance with various aspects of the present invention.

In general, the term "bridging" as used herein refers to the general act of passing data from one data form to another data form (e.g., from one application to another application), not necessarily populating data field windows with the passed data to display the passed data as described in the example of FIG. 6. However, populating may be a part of the bridging/passing process in certain instances, for example, as described in the example of FIG. 6. For example, data may be passed or bridged into one application from another application via standard non-populating interface methods such as shared memory, invoking a DDE call, command line, and others. Otherwise, data may be passed or bridged from a first data form to a second data form by directly populating the second data form (e.g., data field windows).

In summary, embodiments of the present invention provide a system and method for generating text data from graphical image information of a first data form and passing (e.g., populating) the generated text data into another data form. Optical character reading techniques are used to generate the text data from the graphical image data.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiments disclosed, but that the invention will include all embodiments falling within the scope of the appended claims.

What is claimed is:

1. A computer-implemented method for automatically generating and bridging data to a current data form of interest in response to searching an operating system, said method comprising:
    a computer-based platform automatically obtaining search criteria data from a current data form of interest;
    said computer-based platform automatically searching an operating system for at least one other data form having first data that match said search criteria data to identify any matching data forms;
    said computer-based platform automatically performing an image capture operation on at least one predefined area of said any matching data forms to form at least one captured image, wherein said at least one predefined area is a subset of an entire area of said any matching data forms that is predefined in at least one of a definition file stored in memory on said computer-based platform and an operating system of said computer-based platform before performing said method step of obtaining search criteria;

said computer-based platform automatically performing an optical character reading operation on said at least one captured image to generate at least one instance of second data, wherein associated information to be obtained from and a location of said at least one instance of said second data within said predefined area are also predefined in said at least one of a definition file and an operating system; and said computer-based platform automatically passing said at least one instance of second data to said current data form of interest, wherein said current data form of interest is capable of being presented in a window by said operating system.

2. The method of claim 1 wherein said search criteria data comprises a string of characters.

3. The method of claim 1 wherein said search criteria data comprises at least one of name data, window class data, and control identifier data.

4. The method of claim 1 wherein said second data comprises alphabetic text data.

5. The method of claim 1 wherein said second data comprises numeric text data.

6. The method of claim 1 wherein said second data comprises alpha-numeric text data.

7. The method of claim 1 wherein said current data form of interest comprises a window.

8. The method of claim 1 wherein said at least one other data form comprises a window.

9. The method of claim 1 further comprising said computer-based platform automatically activating said at least one other data form.

10. The method of claim 1 further comprising said computer-based platform automatically launching and activating said at least one other data form.

11. The method of claim 1 further comprising said computer-based platform automatically displaying an image of said at least one other data form.

12. The method of claim 1 further comprising said computer-based platform automatically displaying a message when there is not at least one other data form having first data that match said search criteria data.

13. The method of claim 1 wherein said step of performing an image capture operation comprises performing a print screen operation.

14. The method of claim 1 wherein said passing said at least one instance of second data to said current data form of interest includes populating said current data form of interest with said second data for display.

15. A system for automatically generating and bridging data to a current data form of interest in response to searching an operating system of said system, said system comprising a computer-based platform, having at least one hardware-based processor capable of running at least one functional software module, configured for:

automatically obtaining search criteria data from a current data form of interest;

automatically searching an operating system for other data forms having first data that match said search criteria data to identify any matching data forms;

automatically performing an image capture operation on at least one predefined area of said any matching data forms to form at least one captured image, wherein said at least one predefined area is a subset of an entire area of said any matching data forms that is predefined in at least one of a definition file stored in memory on said computer-based platform and an operating system of said computer-based platform before obtaining said search criteria;

automatically performing an optical character reading operation on said at least one captured image to generate at least one instance of second data, wherein associated information to be obtained from and a location of said at least one instance of said second data within said predefined area are also predefined in said at least one of a definition file and an operating system; and automatically passing said at least one instance of second data to said current data form of interest, wherein said current data form of interest is capable of being presented in a window by said operating system.

16. The system of claim 15 wherein said search criteria data comprises a string of characters.

17. The system of claim 15 wherein said search criteria data comprises at least one of name data, window class data, and control identifier data.

18. The system of claim 15 wherein said second data comprises alphabetic text data.

19. The system of claim 15 wherein said second data comprises numeric text data.

20. The system of claim 15 wherein said second data comprises alpha-numeric text data.

21. The system of claim 15 wherein said current data form of interest comprises a window.

22. The system of claim 15 wherein said at least one other data form comprises a window.

23. The system of claim 15 wherein said computer-based platform is further configured for activating said at least one other data form.

24. The system of claim 15 wherein said computer-based platform is further configured for launching and activating said at least one other data form.

25. The system of claim 15 wherein said computer-based platform is further configured for displaying an image of said at least one other data form.

26. The system of claim 15 wherein said computer-based platform is further configured for displaying a message when there is not at least one other data form having first data that match said search criteria data.

27. The system of claim 15 wherein said performing an image capture operation comprises performing a print screen operation.

28. The system of claim 15 wherein said passing said at least one instance of second data to said current data form of interest includes populating said current data form of interest with said second data for display.

* * * * *